US007706547B2

(12) United States Patent
Luo et al.

(10) Patent No.: US 7,706,547 B2
(45) Date of Patent: Apr. 27, 2010

(54) SYSTEM AND METHOD FOR NOISE CANCELLATION

(75) Inventors: Huageng Luo, Clifton Park, NY (US); Peggy Lynn Baehmann, Glenville, NY (US); Gary Randall Barnes, Delanson, NY (US); Robert John Naumiec, Clifton Park, NY (US); Richard Nils Dawson, Voorheesville, NY (US)

(73) Assignee: General Electric Company, Niskayuna, NY (US)

( * ) Notice: Subject to any disclaimer, the term of this patent is extended or adjusted under 35 U.S.C. 154(b) by 2261 days.

(21) Appl. No.: 10/315,983

(22) Filed: Dec. 11, 2002

(65) Prior Publication Data

US 2004/0114768 A1 Jun. 17, 2004

(51) Int. Cl.
*A61F 11/06* (2006.01)
*G10K 11/16* (2006.01)
*H03B 29/00* (2006.01)

(52) U.S. Cl. .................... 381/71.8; 381/71.1; 381/71.9; 381/71.13

(58) Field of Classification Search ..... 381/71.1–71.14, 381/72, 86; 181/206, 224
See application file for complete search history.

(56) References Cited

U.S. PATENT DOCUMENTS 5,511,127 A 4/1996 Warnaka
5,636,287 A 6/1997 Kubli et al.
5,692,052 A * 11/1997 Tanaka et al. .............. 381/71.9
5,910,993 A 6/1999 Aoki et al.
6,201,872 B1 3/2001 Hersh et al.
6,208,057 B1 3/2001 Schultz et al.
6,244,817 B1 6/2001 Ngo
6,901,147 B1 * 5/2005 Enamito et al. ............ 381/71.4
2003/0016833 A1 * 1/2003 Harvey ...................... 381/71.5
2003/0079937 A1 * 5/2003 Vaishya ...................... 181/206

* cited by examiner

*Primary Examiner*—Xu Mei
(74) *Attorney, Agent, or Firm*—Ann M. Agosti

(57) ABSTRACT

The invention is directed to a system and method for noise cancellation for an apparatus such as an electric motors or generator. The system may comprise a plurality of actuators, a plurality of phase controllers, each phase controller receiving an input signal representing a movement of an apparatus and outputting an output signal based on the input signal and at least one predetermined phase shift, and a plurality of amplifiers, each amplifier receiving an output signal from one of the phase controllers and outputting an amplified signal to drive one of the actuators. The method may comprise the steps of generating a first signal representing a movement of the apparatus, generating at least one second signal based on (a) the first signal, (b) at least one predetermined phase shift, and (c) at least one predetermined amplitude, and driving at least one actuator with the at least one second signal.

21 Claims, 8 Drawing Sheets

SYSTEM AND METHOD FOR NOISE CANCELLATION

BACKGROUND OF THE INVENTION

The present invention relates generally to the field of noise cancellation and more particularly to a system and method for noise cancellation in apparatus such as electric motors and generators.

Electric motors and generators generate a substantial amount of tonal noise during operation. In air-cooled generators, for example, the excitation of the tonal noise comes from two major sources: the electromagnetic force and the rotor jets. The noise from the air jets is typically the main source of tonal noise. The air jets create a tonal noise at a fundamental frequency that equals twice the rotational frequency of the rotor. For example, in a two-pole 60 Hz power generator, the fundamental tonal noise has a frequency of 120 Hz. Because of its particular frequency and amplitude, the fundamental tonal noise may be especially annoying to human ear perception.

To meet customer specifications or regulatory requirements, a number of solutions exist to reduce the repetitive noise produced by an electric motor or generator. One approach is to build acoustic walls around the motor or generator so that it becomes isolated in a sound-proof housing. However, this solution is usually expensive and may not always be feasible to practice. Another approach is to attach acoustic panels inside the stator frame or to cover the outside of the motor or generator with acoustic blankets. Due to the fact that the motor or generator surface cannot be fully covered, the noise reduction effect is not as good as that from the surrounding walls.

Other noise reduction solutions focus on active noise cancellation, which involves actively detecting the amplitude, frequency and phase of each of the component waves of the noise in real time, and through complex feedback looped circuitry, generating waves or vibrations of similar amplitudes, frequencies and 180-degree different phase angles (opposite phases), to cancel out the effect of the noise waves or vibrations. However, the active noise cancellation approach usually involves a complicated setup of input sensors, feedback loop logic, and output acoustic sources. Thus, active noise cancellation is usually expensive to implement.

BRIEF SUMMARY OF THE INVENTION

The present invention is directed to a system and method for noise cancellation for apparatus such as electric motors or generators that overcome these and other drawbacks of known systems and methods.

According to one embodiment, the invention relates to a noise cancellation system comprising at least one actuator, and means for receiving a first signal representing a movement of an apparatus in operation and for generating at least one second signal based on the first signal, at least one predetermined phase shift, and at least one predetermined amplitude, wherein the at least one second signal drives the at least one actuator.

According to another embodiment, the invention relates to a method for noise cancellation for an apparatus, the method comprising the steps of generating a first signal representing a movement of the apparatus, generating at least one second signal based on the first signal, at least one predetermined phase shift, and at least one predetermined amplitude, and driving at least one actuator with the at least one second signal.

Exemplary embodiments of the invention can provide a low cost, standalone noise reduction system for effectively reducing noise such as the tonal noise of an electric motor or generator.

It is another advantage of exemplary embodiments of the present invention to use a phase signal output directly from an electric motor or generator to generate noise canceling acoustic waves that may be targeted at the tonal noise at the fundamental or higher order frequency.

Another advantage of exemplary embodiments of the present invention is that predetermined phase angles and amplitudes for the generation of noise canceling acoustic waves can be used, which eliminates the need for sensors and feedback loops. Exemplary embodiments of the invention can thus provide what may be termed "semi-active" noise cancellation.

DETAILED DESCRIPTION OF THE INVENTION

Figure 1:
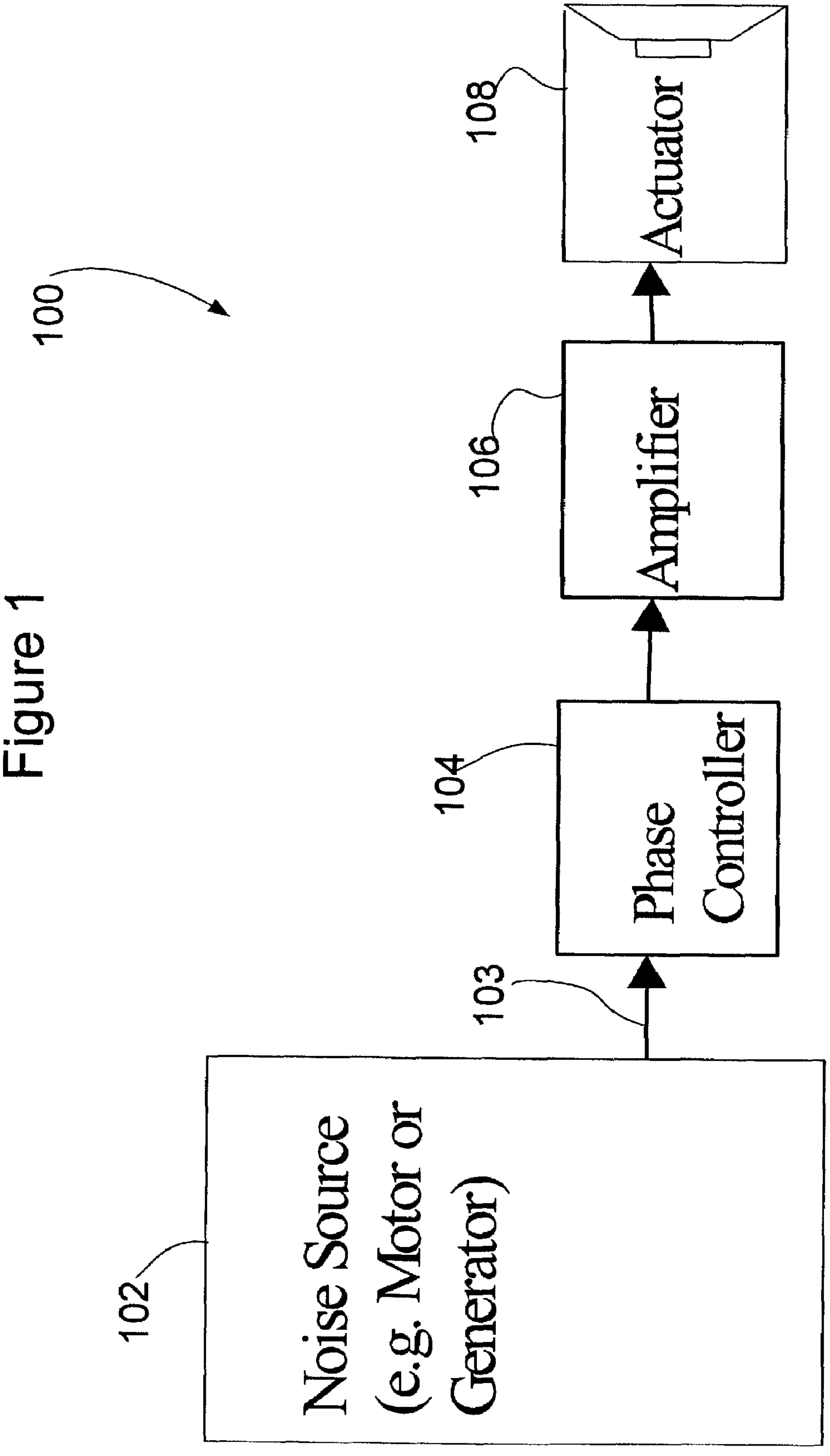
FIG. 1 is a schematic representation of a noise cancellation system according to an exemplary embodiment of the invention.

FIG. 1 is a schematic representation of a semi-active noise cancellation system 100 and its operation, according to an exemplar embodiment of the invention. As shown in FIG. 1, the noise cancellation system 100 comprises a phase controller 104, a signal amplifier 106, and an actuator 108.

FIG. 1 also shows the noise source 102. By way of example, the noise source 102 may be an electric motor or power generator that is stably operating and producing a repetitive noise. According to a particular example, the noise source 102 may be a two-pole 60 Hz power generator that produces over 20 dB of tonal noise above the broadband noise background during operation. According to another exemplary embodiment of the invention, the noise source 102 may be an aircraft driven by propellers that are rotating at a relatively fixed speed.

Figure 7:
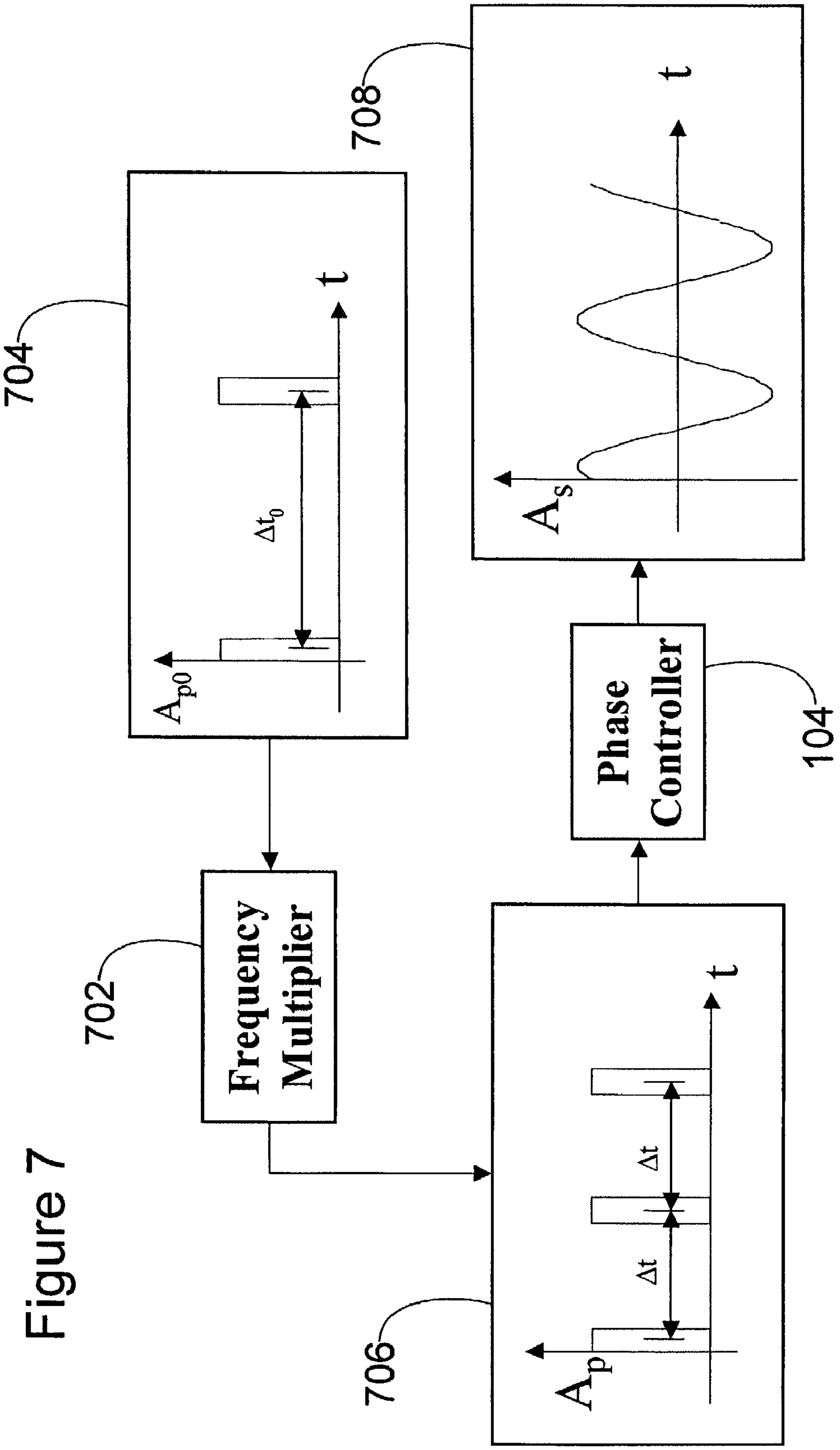
FIG. 7 is an illustration of the operation of a frequency multiplier and phase controller according to one embodiment of the present invention.

The phase controller 104 is a signal-processing device. According to one embodiment of the invention, the phase controller 104 may receive an input signal comprising pulses with a particular frequency $f=1/\Delta t$ and generate an output signal that is a sinusoidal wave with a frequency f and a desired phase angle $\phi$. FIG. 7 shows an example of the input and output to the phase controller 104. As shown in FIG. 7, the input signal 706 to the phase controller 104 may be a pulse with frequency $f=1/\Delta t$. The phase controller 104 may also receive as input a desired phase angle $\phi$. For example, the user may program the desired phase angle $\phi$ into the phase controller 104. The output signal 708 in FIG. 7 is a sinusoidal wave with frequency f and phase $\phi$.

Also shown in FIG. 7 is a frequency multiplier 702. A frequency multiplier is a signal-processing device that may take an input signal 704 that has a frequency $f_0=1/\Delta t_0$, multiply this frequency by a user-specified factor, and generate an output signal 706 that has a new frequency $f=1/\Delta t$, which is a multiple or fraction of the input frequency $f_0$. A frequency multiplier may or may not be included in combination with a phase controller for noise cancellation in accordance with exemplary embodiments of the present invention.

Referring again to FIG. 1, the signal amplifier 106 is a signal-processing device that may modify its input signal to have a predetermined amplitude. The signal amplifier 106 may output a signal suitable to drive the actuator 108. According to one embodiment of the invention, the signal amplifier 106 may be an audio signal amplifier that is capable of receiving an input sinusoidal signal, linearly amplifying it, and generating an output sinusoidal signal to drive a speaker.

The actuator 108 is a device that may generate acoustic vibration, for example. According to one embodiment of the invention, the actuator 108 may be a loudspeaker that produces a human-audible sound with an amplitude, a frequency and a phase angle that are based on its driving signal. According to another embodiment of the invention, the actuator 108 may be a vibrating plate supported by piezo wafers or piezo stacks that are controlled by a driving signal.

An example of the operation of the noise reduction system 100 will now be described. For purposes of illustration, the noise source 102 may be an electric generator in stable operation. It produces, among other things, a repetitive noise that is represented as waveform 202 in the graph of FIG. 2.

As shown in FIG. 1, the phase controller 104 is connected to the noise source 102 (the generator in this example) by a line 103. More particularly, the line 103 may be connected to a terminal on the generator which outputs a once per revolution (1/rev) pulse signal of the generator rotor. The generator may include, for example, a sensor which senses the rotation of its rotor and which outputs a pulse signal representing the rotation of the rotor. This signal, sometimes referred to as a "keyphaser signal," may take the form shown in FIG. 7, e.g., a pulse signal 704 having a period which matches the period of rotation of the rotor. The other end of the line 103 is connected to an input terminal of the phase controller 104 so that the phase controller receives the phase signal from the generator. As will be appreciated by those skilled in the art, other configurations may be implemented. For example, the phase signal input to the phase controller 104 may be generated by other sensors which sense the movement of the noise source 102.

The phase controller 104 outputs a signal with a frequency based on the input signal to the phase controller 104. For example, if the phase controller 104 receives as input the keyphaser signal from a generator, the phase controller 104 may output a signal having a frequency matching the frequency of the keyphaser signal. Alternatively, by sending the input signal through a frequency multiplier 702 first, the phase controller 104 may output a signal having a frequency which is a multiple or fraction of the frequency of the keyphaser signal 704. For example, in the case of a generator, a 60 Hz keyphaser signal 704 may be fed to a frequency multiplier 702 which doubles the frequency to 120 Hz. The phase controller receives the 120 Hz input pulse signal and outputs a 120 Hz sinusoidal wave.

Figure 2:
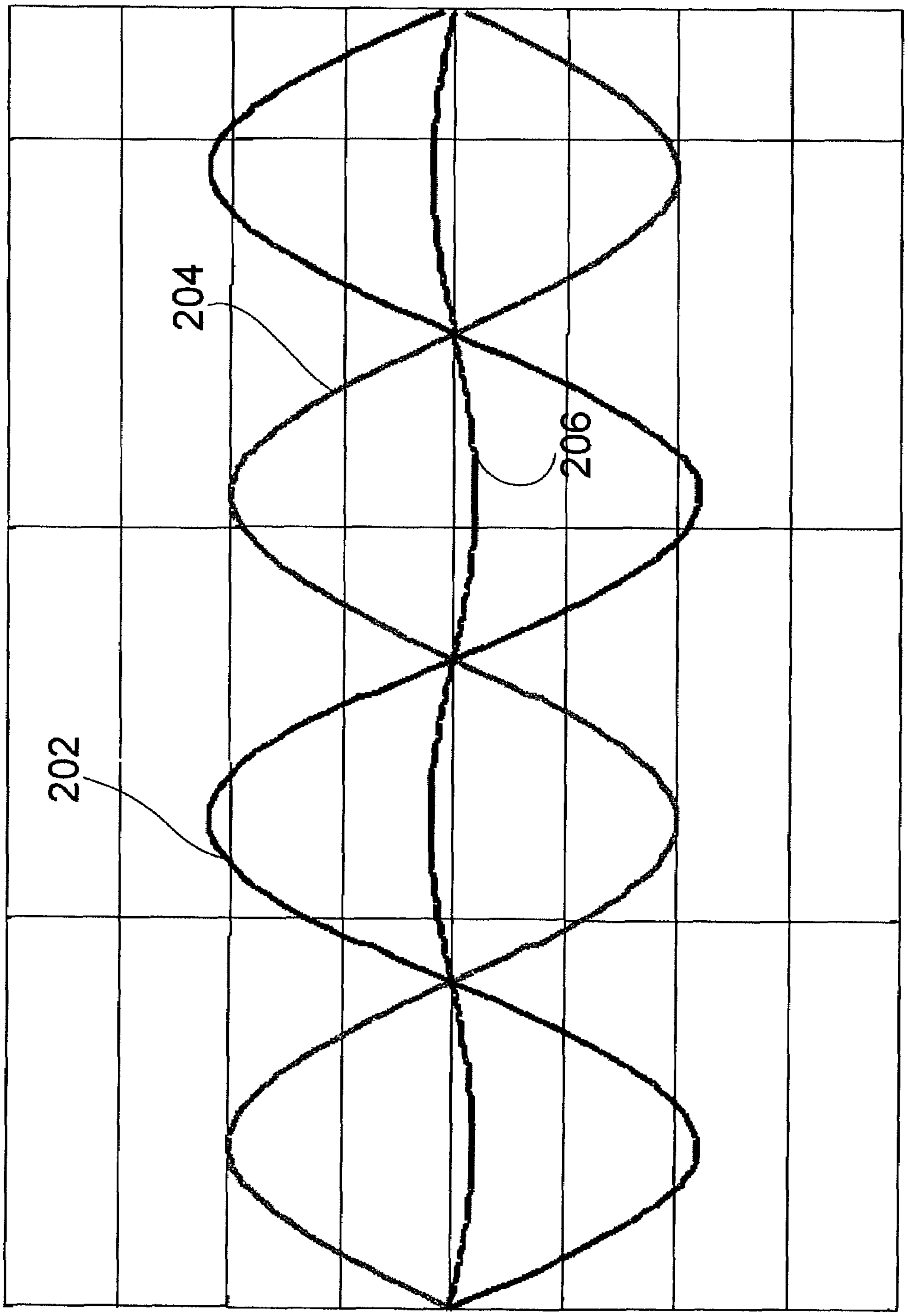
FIG. 2 is a graph showing noise cancellation according to an exemplary embodiment of the invention.

The phase controller 104 may also generate its output signal based on a desired phase angle. For example, the phase controller 104 may allow a user to input a desired phase angle $\phi$. According to one embodiment of the invention, the phase controller 104 may allow a user to set the output signal to a desired phase angle by turning a knob on the hardware device. The phase controller 104 shifts the output signal by the desired phase angle $\phi$. For example, the phase controller may apply a desired phase shift to generate a wave 204, as shown in FIG. 2, which is about 180° out of phase with wave 202.

The signal amplifier 106 amplifies the output signal from the phase controller 104 to a predetermined amplitude and drives the actuator (e.g., speaker) 108 to generate a sound wave 204. The amplitude may be selected, for example, so that it substantially matches the amplitude of the wave 202 to be cancelled. The combined effect of wave 202 and wave 204 is represented as wave 206. Due to the cancellation between the noise source and the wave from the actuator, the resultant wave 206 has a much smaller amplitude than the original wave 202.

Figure 5:
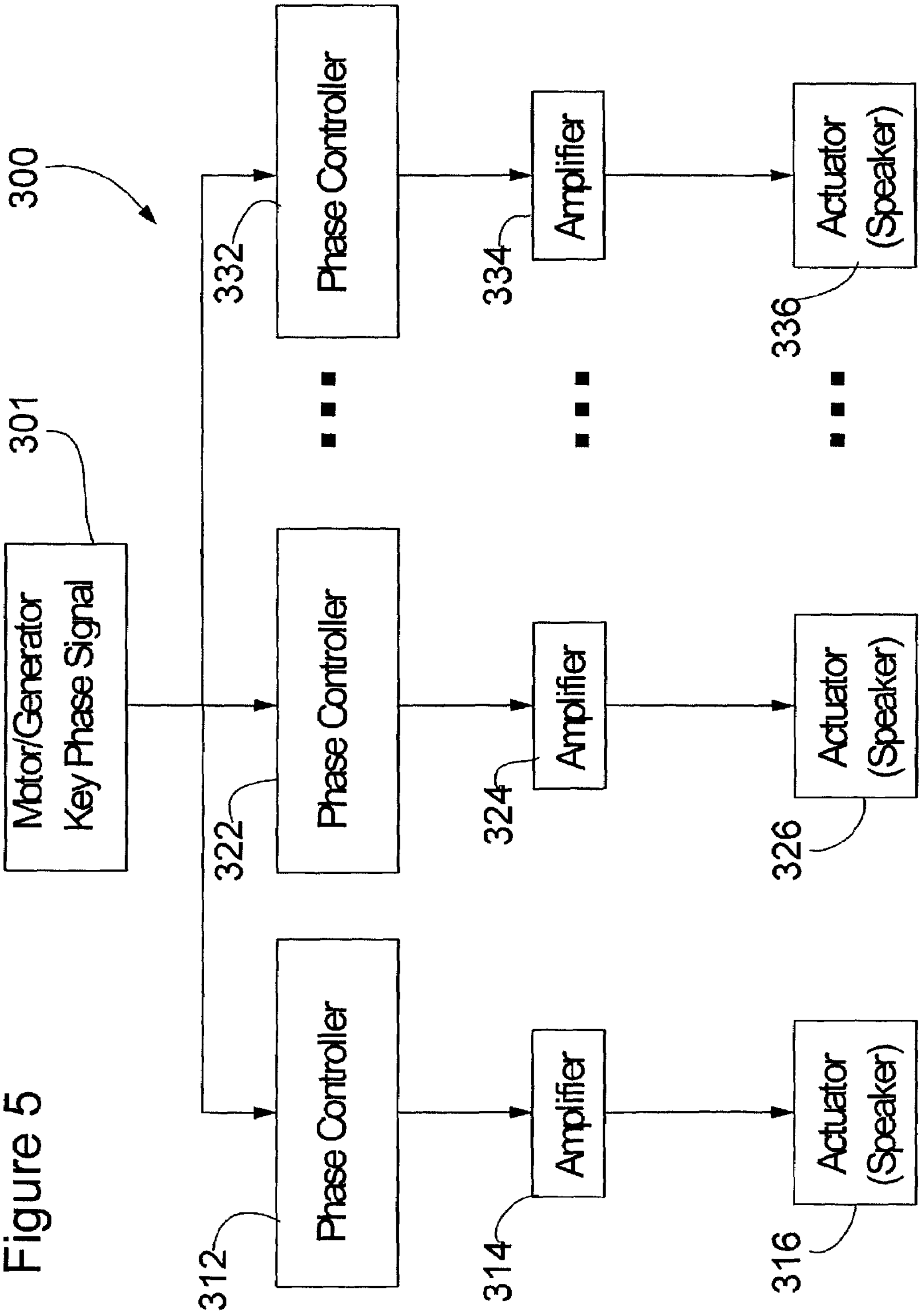
FIG. 5 is a schematic representation of a noise cancellation system, according to another embodiment of the present invention.

According to other embodiments of the invention, a noise cancellation system may comprise more than one phase controller, amplifier and actuator. FIG. 5 is a schematic representation of such a noise cancellation system 300 according to an exemplary embodiment of the invention. As shown in FIG. 5, each phase controller 312, 322, 332 is connected to receive the phase signal 704 from the electric motor or generator 301. If desired, a frequency multiplier can be provided between the generator and the phase controllers. In order to achieve the desired noise reduction effects, the multiple actuators 316, 326, 336 may be positioned based on the position of the noise source 301 and its noise distribution.

Figure 3:
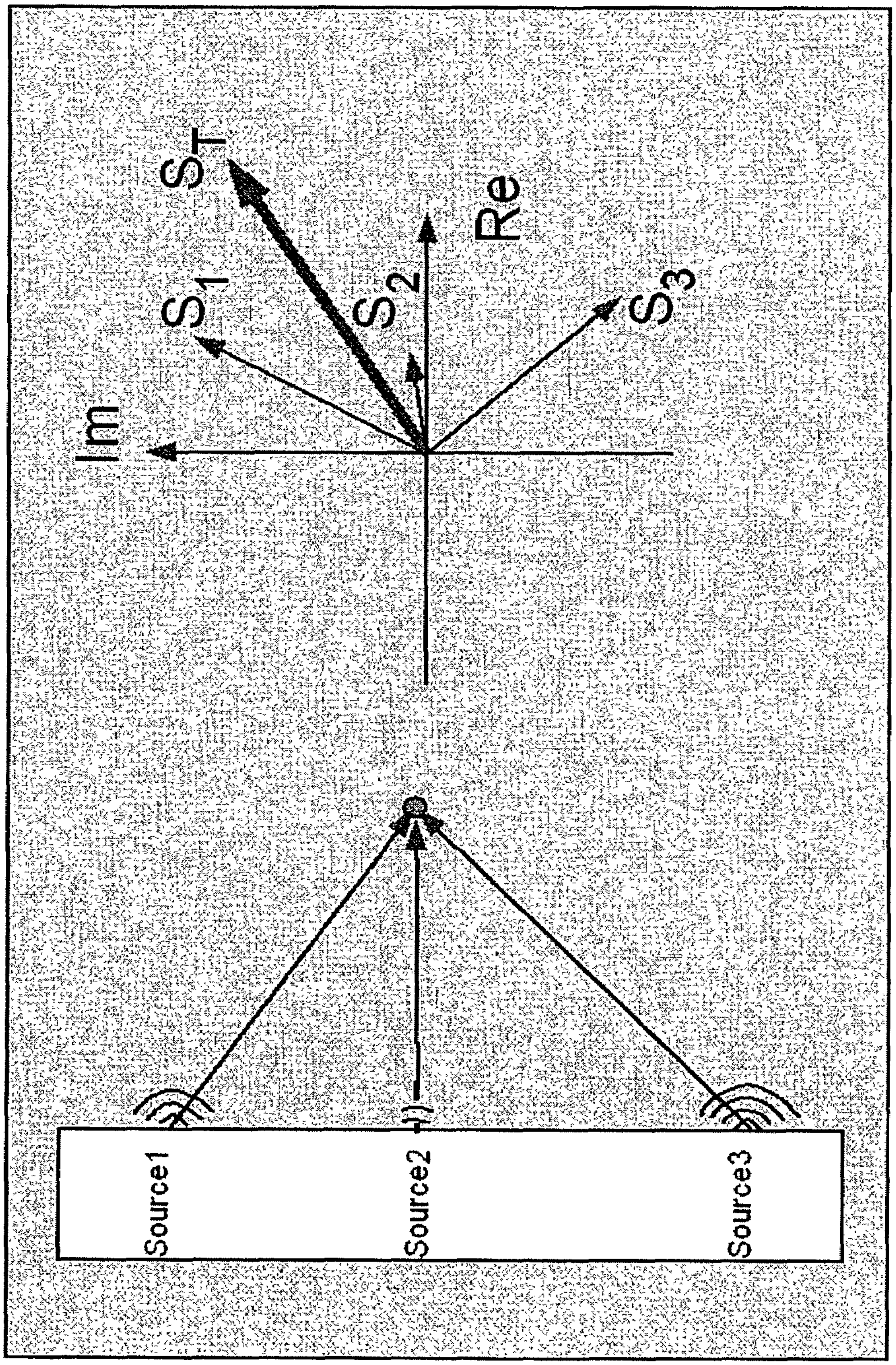
FIGS. 3 and 4 illustrate the operation of a noise cancellation system according to an exemplary embodiment of the invention.
Figure 4:
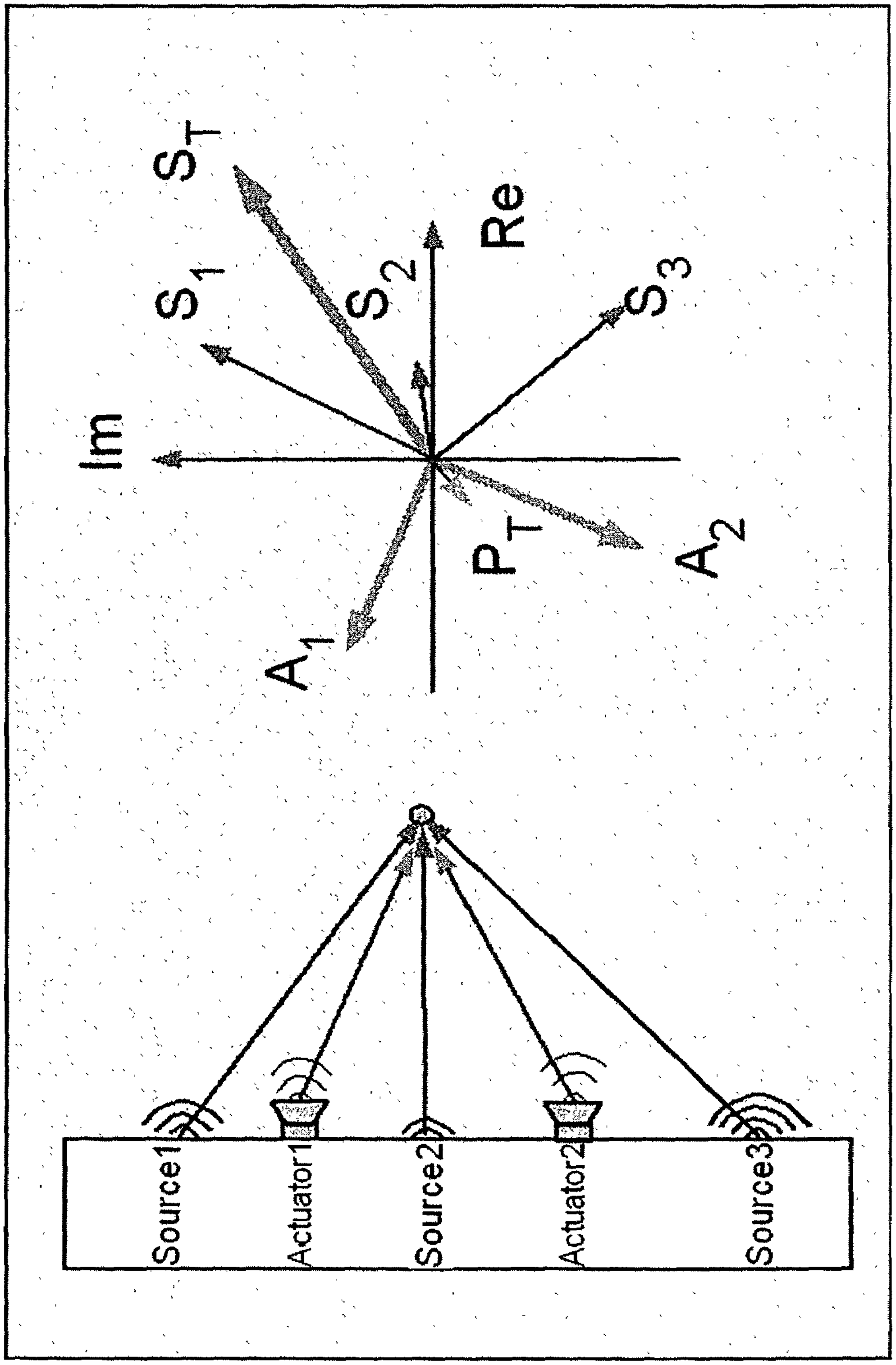

FIGS. 3 and 4 illustrate the operation of a semi-active noise cancellation system having multiple actuators, amplifiers, and phase controllers. As shown in FIG. 3, the noise of a machine such as an electric motor or generator may be modeled as multiple noise sources. As illustrated in FIG. 3, for example, the noise may be modeled as source 1, source 2, and source 3. The noise signals detected at the detection point may be represented in vector form as $S_1$, $S_2$ and $S_3$, respectively. The vector sum of $S_1$, $S_2$ and $S_3$ is $S_T$, which is representative of the total noise from the machine. Multiple actuators may be included to reduce the total noise. As illustrated in FIG. 4, for example, two actuators, actuator 1 and actuator 2, are included. The sound signals from actuator 1 and actuator 2 are represented in vector form as $A_1$ and $A_2$. The total vector sum of $S_1$, $S_2$, $S_3$, $A_1$ and $A_2$ is $P_T$, which is representative of the total noise from the generator and the actuators. As shown in FIG. 4, the amplitudes and phase angles of $A_1$, and $A_2$ may be chosen such that $P_T$ has a significantly smaller amplitude than $S_T$. A noise cancellation method involving multiple actuators will now be described with reference to FIG. 6.

Figure 6:
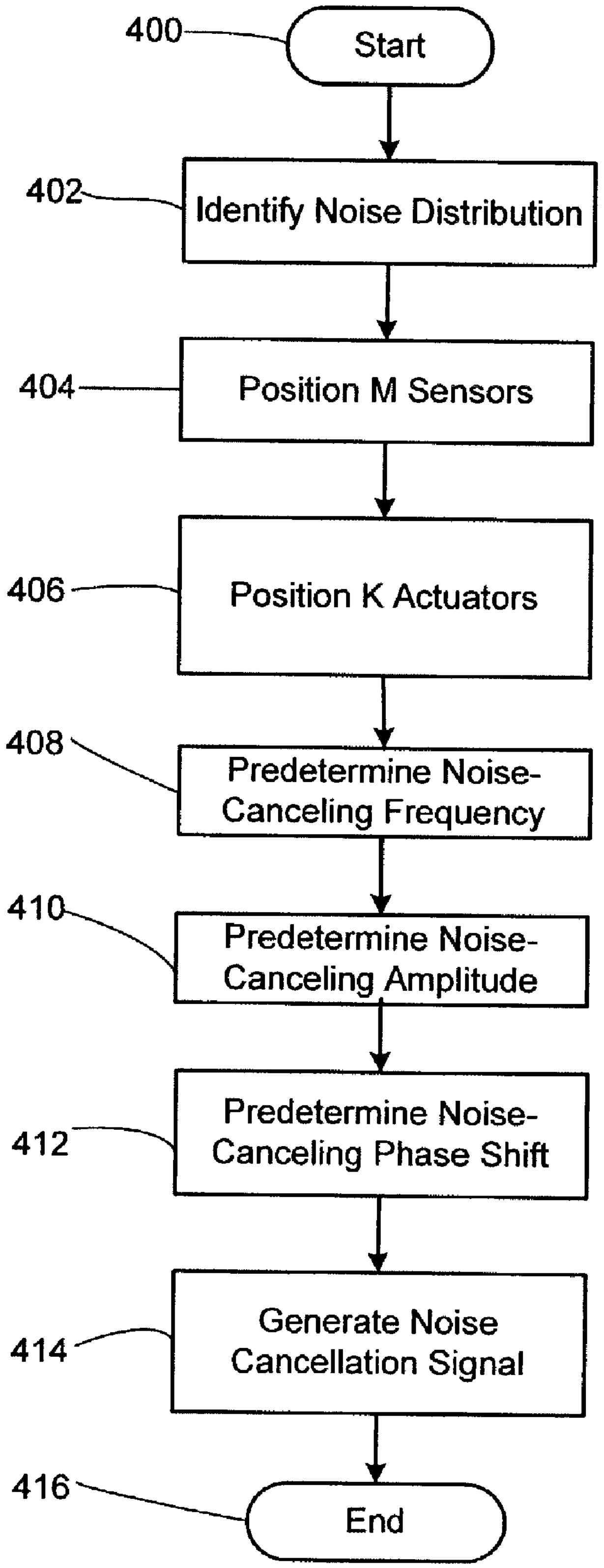
FIG. 6 is a flow chart illustrating a method for semi-active noise cancellation according to one embodiment of the present invention.

FIG. 6 is a flow chart illustrating a method for semi-active noise cancellation according to one embodiment of the present invention. For purposes of illustration, the method will be described in terms of implementing a noise cancellation system for a power generator. However, it should be understood that the invention is also applicable to other noise-producing apparatus, such as electric motors and propeller-driven aircraft, for example.

The method starts at step 400. At step 402, a noise distribution in the vicinity of the power generator is determined. According to one embodiment, the noise distribution may be determined by conducting a sound survey. Sensors (e.g., microphones) may be positioned in the vicinity of the generator to detect noise levels at various locations around the generator. The detection results may be represented in the form of a sound map. The sound map may take the form of a map of sound intensity at a particular frequency, e.g., 120 Hz, at various coordinates around the generator. The sound map may be displayed, for example, on an x-y grid using various colors to represent sound intensity at each position. The sound map thus allows the user to easily identify the regions on or around the generator where the intensity of the noise is the greatest.

At step 404, M noise sensors are positioned around the generator. M is an integer indicating the number of noise sensors. A noise sensor may be a device such as a microphone capable of detecting acoustic vibration and generating an electrical output signal representative of its detection, for example. In this exemplary method, the noise sensors are used for calibration purposes. They are not a necessary part of the final operating system for noise cancellation.

The user may select the positions of the noise sensors based on the noise distribution near the generator. According to one example, the noise sensors may be positioned at or near the M most noisy spots which have been determined from the sound map. According to another example, the positioning of noise sensors may be selected based on desired noise reduction requirements. For example, a customer may request that the control panel side of the generator have a noise level lower than a certain value. In that case, the sensors may be positioned along the side of the generator where the noise needs to be reduced the most.

At step 406, K actuators are positioned. K is an integer indicating the number of actuators. Typically, each actuator is connected to an associated phase controller and signal amplifier in a set. Each phase controller may be connected to the generator, either directly or through a frequency multiplier, to receive its keyphaser signal or once-per-revolution signal as an input. Alternatively, according to other embodiments of the invention, other devices may be utilized to reconstruct and generate signals that are representative of the movement of the generator and to send the signals into the phase controllers. Each phase controller is connected to a signal amplifier, which may amplify the signals received from the phase controller to a desired amplitude and use the amplified signals to drive an actuator, such as a loudspeaker. The actuators are positioned to generate the desired noise-reduction effect. For example, in order to reduce noise on one side of the generator, actuators may be positioned to direct sounds to the particular noise-concentrated spots on that side of the generator. The user may use the sound map to select the desired positions of the actuators. For example, the user can place the actuators at or near the regions of highest intensity noise.

At step 408, a desired noise canceling frequency is selected. The noise canceling frequency may be the same as or a multiple or fraction of the keyphaser signal from the generator. For example, with a generator having a rotor which rotates at 60 Hz, the noise canceling frequency may be chosen to be 120 Hz to cancel tonal noise of the generator at this frequency. If desired, a frequency multiplier may be used to modify, e.g. double, the frequency of the keyphaser signal before it is sent to the phase controller.

At step 410, a desired noise canceling amplitude for each set of phase controller, amplifier and actuator is selected. An amplitude suitable for noise cancellation may be determined based on the noise distribution near the generator. For example, to target the fundamental tone of the generator's tonal noise, a typical amplitude of this type of noise may be measured and used as a noise canceling amplitude. For a noise cancellation system and method with multiple actuators, the desired amplitudes may be determined with a cost function J, described below. The selected amplitude for each actuator is produced by its corresponding signal amplifier. Each signal amplifier may be configured to produce the desired amplitude for each actuator. The amplitude values for different actuators may be different.

At step 412, an appropriate noise-canceling phase angle for each set of phase controller, amplifier and actuator is determined. According to one embodiment of the invention, this phase angles, as well as the amplitudes, may be determined by the following process.

First, the responses of the M noise sensors to the noise of the generator in operation is recorded without the actuators running. The noise level is measured as $$\{p_{0i}\}^T=[p_{01},p_{02}, \ldots , p_{0M}]$$

where $p_{01}$ represents the noise level measured by the first noise sensor, $p_{02}$ represents the noise level measured by the second noise sensor, and so on, and $p_{0M}$ represents the noise level measured by the $M^{th}$ noise sensor.

Second, the K actuators are turned on and the phase on the $k^{th}$ actuator is set at $\phi_k$. A series of noise levels recorded by the M sensors are $$\{p_{1i}\}^T = \{p_{0i}\}^T + \sum_{k=1}^{K} e^{j\phi_k} T_{ki} = \{p_{0i}\}^T + \{e^{j\phi_k}\}^T [T_{ki}]$$

where $$\{p_{1i}\}^T=[p_{11},p_{12}, \ldots , p_{1M}]$$

with $p_{11}$ representing the new noise level measured by the first noise sensor, $p_{12}$ representing the new noise level measured by the second noise sensor, and so on, and $p_{1M}$ representing the new noise level measured by the $M^{th}$ noise sensor. $T_{ki}$ is a transfer function from the $k^{th}$ actuator to the $i^{th}$ sensor, which relates the noise level change, $p_i$, at the $i^{th}$ sensor in response to a phase angle change $\phi_k$ at the $k^{th}$ actuator by $$\{p_i\}^T=\{p_{1i}\}^T-\{p_{0i}\}^T=\{e^{j\phi k}\}^T[T_{ki}].$$

Next, a cost function may be defined as $$\begin{aligned} J(\phi_1, \cdots, \phi_K) &= \sum_{i=1}^{M} p_{1i}^2 \\ &= \sum_{i=1}^{M} p_{0i}^2 + \{p_{0i}\}^T[T]^T\{e^{j\phi_k}\} + \{e^{j\phi_k}\}^T[T]\{p_{0i}\} + \\ &\quad \{e^{j\phi_k}\}^T[T][T]^T\{e^{j\phi_k}\} \end{aligned}$$

A desired set of phases may be obtained with the cost function J. For example, by minimizing the cost function J, a set of phases for the actuators may be obtained which effectively cancels the noise of the generator. A desired set of amplitudes for multiple actuators may also be determined with the cost function J and the transfer functions $[T_{ki}]$. The amplitudes are the magnitudes of the transfer function matrix [T] column vector.

According to other embodiments of the invention, the appropriate phases for each actuator may also be determined empirically by a trial-and-error approach, for example if only a small number of actuators is used. The set of phase angles and amplitudes chosen by the user may be that set which minimizes the overall noise level or that set which achieves some other objective of the user, such as reduction of noise in only a selected region near the machine.

After the amplitudes, phases, and frequency for each actuator have been selected and configured, the system can be operated, at step 414. In operation, each phase controller receives a signal, such as the keyphaser signal from a generator, or a frequency-modified version thereof, representing the movement or vibration of the machine causing the noise. For example, the phase controller may receive a signal having a frequency which is a multiple, a fraction, or the same frequency as the frequency of the keyphaser signal. The phase controller outputs a signal, such as a sinusoidal signal, having a frequency which is based on the input signal.

Each phase controller also has received a desired phase, which is typically different from one phase controller to the next. For example, each phase controller may be preprogrammed with a desired phase angle. Each amplifier has been configured to generate an output signal having a predetermined amplitude. The output signal from the amplifier thus has the desired phase, amplitude and frequency to drive the actuator to effect noise reduction.

Exemplary embodiments of the invention can provide effective noise cancellation without requiring sensors and feedback loops to be used during operation. For example, after being configured, the noise cancellation system can be implemented with one or more sets of phase controller, amplifier, actuator by connecting each phase controller, directly or through a frequency multiplier, to the frequency signal generated by the noise making apparatus. Moreover, on a particular product line or product type, the configuration steps, in which the desired frequency multiplier, phase angle, and amplitude are selected for each actuator, can be carried out for one machine, and those values can be used for each machine in the product line. Thus, the noise cancellation system can be implemented in such case by installing the preconfigured set(s) of phase controller, amplifier, actuator on the machine at predetermined locations and connecting the system to the keyphaser signal of the machine, with or without a frequency mulitplier.

Figure 8:
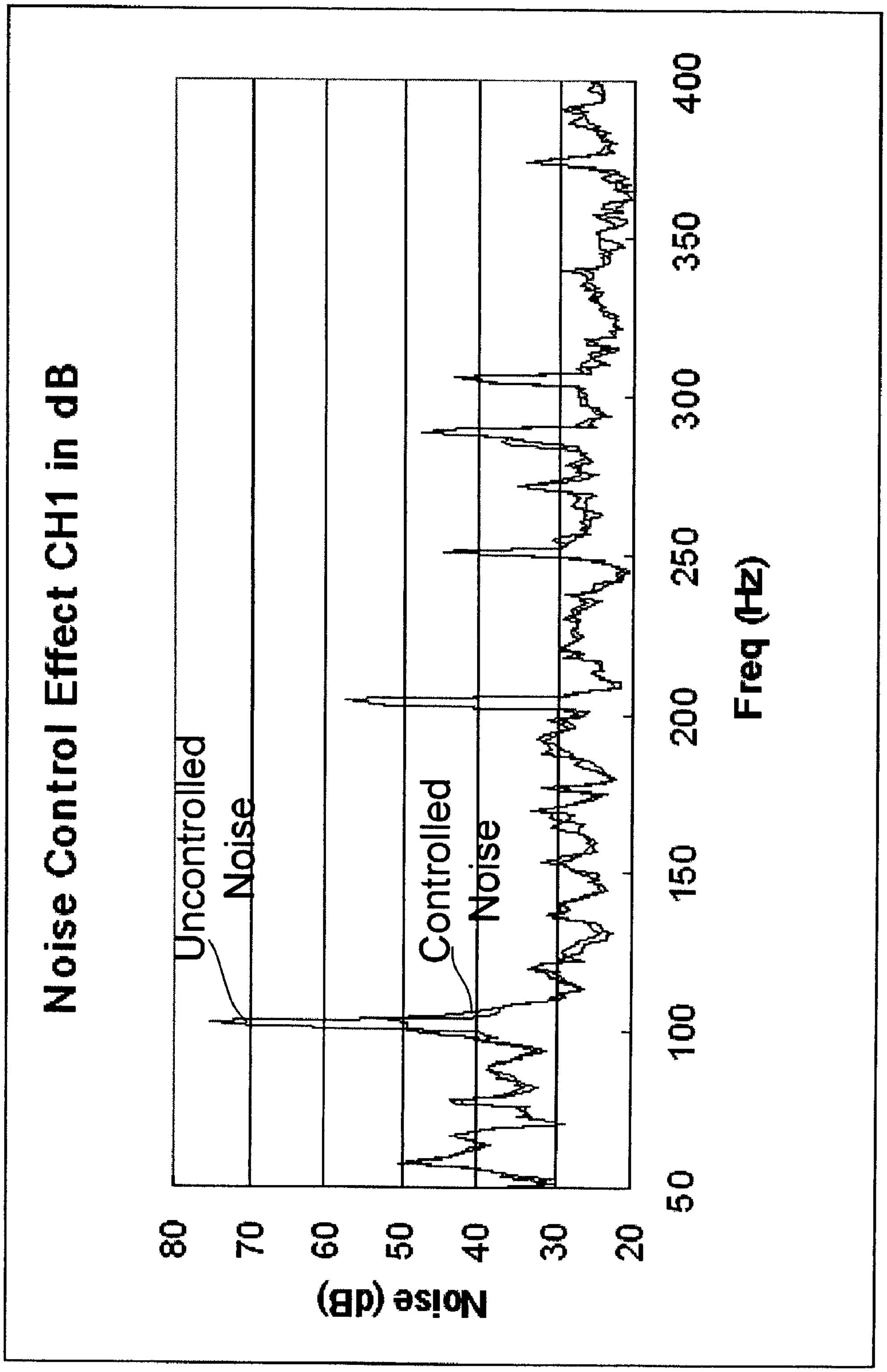
FIG. 8 is a graph showing an example of noise cancellation data from an experimental system.

The principles of the invention have been tested in the laboratory. The noise source was simulated by four six-blade fans with precise speed control. One speaker was used as the actuator. The fan motor once per revolution signal was detected by a magnetic sensor. Since the primary tonal noise is at the fan blade passage frequency, the once per revolution signal was multiplied by 6 with a frequency multiplier to obtain the fundamental noise frequency. The pulse was then converted into a sinusoidal signal with controlled phase. The sinusoidal signal was amplified by an amplifier before being fed to the speaker. The amplitude was adjusted so that the noise amplitude of the speaker alone was approximately equal to the noise generated by the fans. The control effect was measured by a microphone located about five feet away from the actuator and fan plane. A noise reduction effect of about 20 dB at the fan blade passage frequency was achieved, as shown in FIG. 8.

While the foregoing description includes many details and specificities, it is to be understood that these have been included for purposes of explanation only, and are not to be interpreted as limitations of the present invention. For example, the invention may be applied to machines such as a propeller-driven aircraft in addition to motors and generators or may be used to minimize vibration with a vibration shaker as an actuator, for example. In addition, the functions of the phase controller may be carried out by other conventional hardware. Many modifications to the embodiments described above can be made without departing from the spirit and scope of the invention, as is intended to be encompassed by the following claims and their legal equivalents.

What is claimed is:

1. A method for noise cancellation for an apparatus using an actuator including a predetermined desired phase shift and a predetermined desired amplitude, the method comprising the steps of:

generating a first signal representing a movement of the apparatus;

generating a second signal based on (a) the first signal, (b) the predetermined desired phase shift, and (c) the predetermined desired amplitude; and driving the actuator with the second signal, wherein the predetermined desired phase shift and the predetermined desired amplitude are set prior to generating the first signal.

2. The method of claim 1, wherein the second signal comprises a plurality of second signals;

the predetermined phase shift comprises a plurality of predetermined phase shifts;

the actuator comprises a plurality of actuators;

each of the plurality of second signals is generated based on a respective one of the plurality of predetermined phase shifts; and each of the plurality of second signals drives a respective one of the plurality of actuators.

3. The method of claim 2, wherein the predetermined amplitude comprises a plurality of predetermined amplitudes; and each of the plurality of second signals is generated based on one of the plurality of predetermined amplitudes.

4. The method of claim 3, wherein the plurality of predetermined amplitudes are predetermined based on a noise distribution in the vicinity of the apparatus in operation.

5. The method of claim 2, wherein each of the plurality of second signals is sinusoidal.

6. The method of claim 2, wherein the first signal is a square wave.

7. The method of claim 2, wherein the step of generating the first signal comprises:

generating a signal having a frequency with a sensor; and modifying the frequency of the signal generated with the sensor to produce the first signal.

8. The method of claim 7, wherein the first signal has a frequency which is a multiple of the frequency of the signal generated with the sensor.

9. The method of claim 2, wherein the plurality of predetermined phase shifts are predetermined by:

positioning a plurality of sensors such that the sensors sense sound generated by the plurality of actuators;

generating a plurality of third signals with the plurality of sensors, the third signals representing noise from the apparatus in operation;

generating a plurality of fourth signals with the plurality of sensors, the fourth signals representing noise from the plurality of actuators and the apparatus in operation; and calculating a phase shift for each of the actuators based on the third signals and the fourth signals.

10. The method of claim 9, further comprising the step of calculating an amplitude for each of the actuators based on the third signals and the fourth signals.

11. The method of claim 1, wherein the phase shift is predetermined by:

positioning a sensor such that the sensor senses sound generated by the actuator;

generating a third signal with the sensor, the third signal representing noise from the apparatus in operation;

generating a fourth signal with the sensor, the fourth signal representing noise from the actuator and the apparatus in operation; and calculating a phase shift for the actuator based on the third signal and the fourth signal.

12. The method of claim 1, wherein the apparatus is an electric motor.

13. The method of claim 1, wherein the apparatus is an electric generator.

14. The method of claim 1, wherein the apparatus is a propeller-driven aircraft.

15. A method for noise cancellation for an apparatus, the method comprising the steps of:

positioning at least one actuator at a location fixed with respect to the apparatus based on a noise distribution of the apparatus;

providing a phase controller for each of the at least one actuator, wherein the phase controller receives an input signal representing movement of the apparatus in operation, and the phase controller outputs an output signal based on the input signal and having a phase based on a predetermined desired phase shift; and actuating the actuator based on the output signal from the phase controller, wherein the predetermined desired phase shift is set prior to positioning the at least one actuator.

16. The method of claim 15, wherein the input signal is produced by generating a signal having a frequency with a sensor and modifying the frequency of the signal generated with the sensor to produce the input signal.

17. The method of claim 15, further comprising the steps of:

amplifying the output signal from the phase controller by a predetermined amount; and actuating the actuator with the amplified signal.

18. A noise cancellation method comprising the steps of:

measuring an intensity of noise generated by an apparatus in operation;

positioning a plurality of actuators with respect to the apparatus based on the measurement of noise intensity;

determining a plurality of respective phase shifts for each of the plurality of actuators;

determining a plurality of respective amplitudes for each of the plurality of actuators; then generating a first signal which represents a movement of the apparatus in operation;

generating a plurality of second signals based on the first signal, the respective phase shifts, and the respective amplitudes; and driving the plurality of actuators based on the plurality of second signals.

19. A noise cancellation system comprising:

a plurality of actuators;

a plurality of phase controllers, each phase controller configured for receiving an input signal representing a movement of an apparatus and outputting an output signal based on the input signal and at least one predetermined desired phase shift that is set prior to receipt of the input signal; and a plurality of amplifiers, each amplifier for receiving an output signal from one of the phase controllers and outputting an amplified signal to drive one of the actuators.

20. The system of claim 19, wherein the output signals from the phase controller are sinusoidal.

21. The system of claim 20, further comprising a frequency multiplier configured for receiving a signal having a frequency generated by a sensor and modifying the frequency to produce the input signal to the phase controllers.

* * * * *

UNITED STATES PATENT AND TRADEMARK OFFICE

CERTIFICATE OF CORRECTION

PATENT NO. : 7,706,547 B2

APPLICATION NO. : 10/315983

DATED : April 27, 2010

INVENTOR(S) : Luo et al.

It is certified that error appears in the above-identified patent and that said Letters Patent is hereby corrected as shown below:

In Column 6, Lines 23-25, delete "

$$\{p_{1i}\}^T = \{p_{0i}\}^T + \sum_{k=1}^{K} e^{j\phi_k} T_{ki} = \{p_{0i}\}^T + \{e^{j\phi_k}\}^T [T_{ki}]$$

" and insert --

$$\{p_{1i}\}^T = \{p_{0i}\}^T + \sum_{k=1}^{K} e^{j\phi_k} T_{ki} = \{p_{0i}\}^T + \{e^{j\phi_k}\}^T [T_{ki}]$$

--, therefor.

Signed and Sealed this

Thirteenth Day of July, 2010

David J. Kappos

*Director of the United States Patent and Trademark Office*